(12) United States Patent
Hollinshead

(10) Patent No.: US 8,710,063 B2
(45) Date of Patent: Apr. 29, 2014

(54) PURINE COMPOUNDS USED AS CB2 AGONISTS

(75) Inventor: Sean Patrick Hollinshead, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/583,009

(22) PCT Filed: Mar. 30, 2011

(86) PCT No.: PCT/US2011/030412
§ 371 (c)(1),
(2), (4) Date: Sep. 6, 2012

(87) PCT Pub. No.: WO2011/123482
PCT Pub. Date: Oct. 6, 2011

(65) Prior Publication Data
US 2012/0329809 A1    Dec. 27, 2012

Related U.S. Application Data

(60) Provisional application No. 61/319,532, filed on Mar. 31, 2010.

(51) Int. Cl.
*A61K 31/52*    (2006.01)
*C07D 473/34*    (2006.01)

(52) U.S. Cl.
USPC ........................... 514/263.2; 544/264

(58) Field of Classification Search
USPC ........................ 544/264; 514/263.2
See application file for complete search history.

(56) References Cited

U.S. PATENT DOCUMENTS

| | | | |
|---|---|---|---|
| 4,728,644 A | 3/1988 | Yuki et al. | |
| 2003/0139427 A1 | 7/2003 | Castelhano et al. | |
| 2010/0160288 A1* | 6/2010 | Astles et al. | 514/210.18 |

FOREIGN PATENT DOCUMENTS

| | | |
|---|---|---|
| EP | 0300726 | 1/1989 |
| WO | 03/022214 | 3/2003 |
| WO | 2004/037823 | 5/2004 |
| WO | 2005/067546 | 7/2005 |
| WO | 2006/128172 | 11/2006 |
| WO | 2010/019762 | 2/2010 |
| WO | 2010/080306 | 7/2010 |

OTHER PUBLICATIONS

WebMD. Pain Management: Treatment Overview. 2010. <http://www.webmd.com/pain-management/guide/cause-treatments>.*
J Guindon, et al., Cannabinoid CB2 receptors: a therapeutic target for the treatment of inflammatory and neuropathic pain, British Journal of Pharmacology, 2008, vol. 153, No. 2, pp. 319-334.
David A Griffith, et al., Discovery of 1-[9-(4-Chlorophenyl)-8-(2-chlorophenyl)-9H-purin-6-yll-4-ethylamnino-piperidine-4-carboxylic Acid Amide Hydrochloride (CP-945,598), a Novel, Potent, and Selective Cannabinoid Type 1 Receptor Antagonist, Journal of Med. Chem., 2008, vol. 52, No. 2, pp. 234-237.

* cited by examiner

*Primary Examiner* — Golam M M Shameem
*Assistant Examiner* — Laura Daniel
(74) *Attorney, Agent, or Firm* — R. Craig Tucker

(57) ABSTRACT

A compound of the formula:

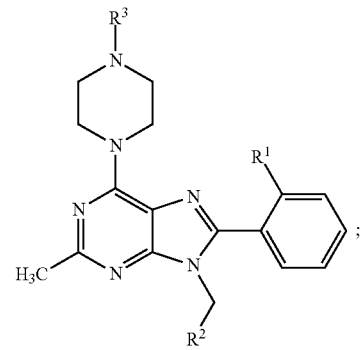

(I)

and pharmaceutical compositions for the treatment of pain.

13 Claims, No Drawings

PURINE COMPOUNDS USED AS CB2 AGONISTS

This application is a United States national phase entry, pursuant to 35 U.S.C. 371, of PCT/US2011/030412, filed Mar. 30, 2011, which claims the benefit of U.S. provisional patent application Ser. No. 61/319,532, filed Mar. 31, 2010.

Cannabinoid receptors $CB_1$ and $CB_2$ belong to the class of G-protein-coupled receptors (GPCRs). $CB_1$ receptors are expressed both centrally and peripherally while $CB_2$ receptors are predominately expressed peripherally, primarily on immune cells and tissues.

The pharmacological and therapeutic potential of the $CB_2$ receptor has been reviewed recently (Br. J. Pharmacol. (2008) 153, 319-334) identifying $CB_2$ as a therapeutic target for the treatment of pain, in particular, inflammatory and neuropathic pain.

$CB_2$ agonists, in particular $CB_2$-selective agonists, provide a target for treating pain with limited centrally mediated side effects.

WO 2004/037823 is directed to purine compounds and use thereof as cannabinoid receptor ligands, in particular as $CB_1$ receptor antagonists.

As a consequence of side effects associated with current oral pharmacological agents, there continues to be a need for the development of alternative therapies for the treatment of pain.

The present invention provides a compound of the formula:

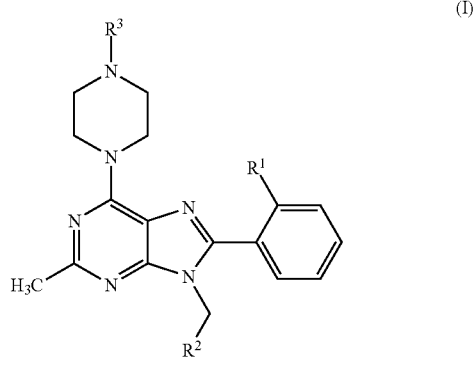

(I)

wherein;
$R^1$ is Cl or $CH_3$;
$R^2$ is C≡N, —$CH_2SO_2CH_3$, —$CONHCH_3$, —$CH_2NR^4R^5$, or —$CH_2C≡N$;
$R^3$ is $C_1$-$C_2$ alkyl, $C_1$-$C_2$ fluoroalkyl or $C(O)CH_3$;
$R^4$ is H, $C(O)CH_3$, $CO_2CH_3$ or $SO_2CH_3$; and
$R^5$ is H or combines with $R^4$ to form pyrrolidin-2-one;
or a pharmaceutically acceptable salt thereof.

Compounds of the present invention have been found to be agonists of the $CB_2$ receptor in vitro. Certain compounds of the present invention exhibit greater potency than existing $CB_2$ agonists. Certain compounds of the present invention are $CB_2$-selective agonists. Certain compounds of the present invention exhibit greater $CB_2$-selectivity than existing $CB_2$ agonists.

The present invention provides a pharmaceutical composition comprising a compound of the present invention, or a pharmaceutically acceptable salt thereof, and a pharmaceutically acceptable diluent or carrier. Further, the present invention provides a pharmaceutical composition comprising a compound of the present invention, or a pharmaceutically acceptable salt thereof, together with a pharmaceutically acceptable diluent or carrier and optionally one or more therapeutic ingredients.

The present invention provides a compound, or a pharmaceutically acceptable salt thereof, for use in therapy. The present invention also provides a compound, or a pharmaceutically acceptable salt thereof for use in the treatment of pain, in particular osteoarthritic pain or migraine. In another aspect of the present invention, there is provided the use of a compound, or a pharmaceutically acceptable salt thereof, for the manufacture of a medicament for the treatment of pain, in particular osteoarthritic pain or migraine.

The present invention provides a method for the treatment of pain, which comprises administering an effective amount of a compound of the present invention, or a pharmaceutically acceptable salt thereof, to a human or animal in need thereof. The present invention also provides a method for the treatment of osteoarthritic pain or migraine, which comprises administering an effective amount of a compound of the present invention, or a pharmaceutically acceptable salt thereof, to a human or animal in need thereof.

It is preferred that the compounds of the present invention be used in the treatment of pain, in particular osteoarthritic pain or migraine.

$CB_2$ receptor agonists have also been identified as having therapeutic potential in the treatment of multiple sclerosis (Br. J. Pharmacol. (2008) 153, 216-225 and J. Biol. Chem. (2008) 283, 13320-13329).

Preferred species of the present invention are compounds of the formula:

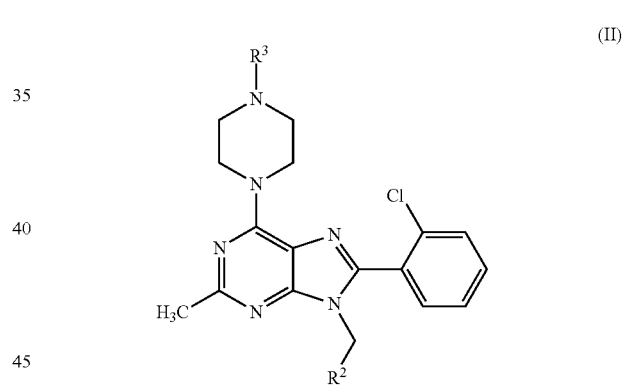

(II)

or a pharmaceutically acceptable salt thereof, wherein $R^2$, $R^3$, $R^4$ and $R^5$ are as defined herein.

Certain classes of compounds of Formula I or II are preferred. The following enumerated selections describe such preferred classes:

1) $R^2$ is —$CH_2SO_2CH_3$, —$CH_2NR^4R^5$ or —$CH_2C≡N$;
2) $R^2$ is —$CH_2SO_2CH_3$;
3) $R^3$ is methyl, ethyl, 2-fluoroethyl or $C(O)CH_3$;
4) $R^3$ is methyl or ethyl;
5) $R^4$ is $C(O)CH_3$ or $CO_2CH_3$;
6) $R^5$ is H;
7) $R^5$ is H and $R^4$ is $C(O)CH_3$ or $CO_2CH_3$;
8) $R^2$ is —$CH_2SO_2CH_3$, —$CH_2NR^4R^5$ or —$CH_2C≡N$; $R^5$ is H and $R^4$ is $C(O)CH_3$ or $CO_2CH_3$;
9) $R^2$ is —$CH_2SO_2CH_3$, —$CH_2NR^4R^5$ or —$CH_2C≡N$; $R^5$ is H; $R^4$ is $C(O)CH_3$ or $CO_2CH_3$; and $R^3$ is methyl, ethyl, 2-fluoroethyl or $C(O)CH_3$;
10) $R^2$ is —$CH_2SO_2CH_3$; $R^3$ is methyl, ethyl, 2-fluoroethyl or $C(O)CH_3$;
11) $R^2$ is —$CH_2SO_2CH_3$; $R^3$ is methyl or ethyl.

Pharmaceutically acceptable salts of each of the compounds of the present invention are contemplated within the scope of the present application.

As used throughout this specification it is to be understood that where a group is qualified by "defined herein" or "herein defined" that said group encompasses the first occurring and broadest definition as well as each and all of the particular definitions of that group.

As used above and throughout the description of the invention, the following terms, unless otherwise indicated will have the following meaning:

As used herein the term $C_1$-$C_2$ alkyl refers to methyl or ethyl.

As used herein the term $C_1$-$C_2$ fluoroalkyl refers to a $C_1$-$C_2$ alkyl group as defined herein, wherein one or more hydrogen is replaced by fluorine and includes, trifluoromethyl, 2-fluoroethyl, 2,2-difluoroethyl and 2,2,2 trifluoroethyl. A preferred $C_1$-$C_2$ fluoroalkyl group is 2-fluoroethyl.

As used herein the term "pharmaceutically acceptable salt" refers to salts of the compounds of the present invention which are substantially non-toxic to living organisms. Such salts and common methodology for preparing them are well known in the art. See, e.g., P. Stahl, et al., Handbook of Pharmaceutical Salts: Properties Selection and Use, (VCHA/Wiley-VCH, 2002); and J. Pharm. Sci. 66, 2-19 (1977). Preferred pharmaceutically acceptable salts are hydrochloride.

Embodiments of the invention include the examples provided herein, and although the example provided may be of one chiral or conformational form, or a salt thereof, further embodiments of the invention include all other stereoisomeric and or conformational forms of the examples described, as well as pharmaceutically acceptable salts thereof.

As used herein the term "$CB_2$-selective agonists" or "$CB_2$-selectivity" refers to compounds having greater potency at $CB_2$ than $CB_1$. Preferably compounds of the present invention exhibit≥50 fold $CB_2$-selectivity. More preferably compounds of the present invention exhibit≥100 fold $CB_2$-selectivity. Most preferably compounds of the present invention exhibit≥500 fold $CB_2$-selectivity.

The compounds of the present invention are preferably formulated as pharmaceutical compositions administered by a variety of routes. Preferably, such compositions are for oral administration. Such pharmaceutical compositions and processes for preparing same are well known in the art. See, e.g., Remington: The Science and Practice of Pharmacy (A. Gennaro, et al., eds., 19$^{th}$ ed., Mack Publishing Co., 1995).

The following Schemes, Preparations, and Examples are provided to better elucidate the practice of the present invention. Suitable reaction conditions for the steps of these Schemes, Preparations, and Examples are well known in the art and appropriate modification of reaction conditions, including substitution of solvents and co-reagents are within the ability of the skilled artisan.

Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. The skilled artisan will appreciate that not all substituents are compatible with all reaction conditions. These compounds may be protected or modified at a convenient point in the synthesis by methods well known in the art.

Suitable protecting groups include those described in T. W. Greene, "Protective Groups in Organic Synthesis", John Wiley and Sons, New York, N.Y., 1991, hereafter referred to as "Greene". Greene indicates appropriate conditions for "protection" and "de-protection" of suitable protecting groups to be used by the skilled artisan.

The intermediates and final products of the present invention may be further purified, if desired by common techniques such as recrystallization or chromatography over solid supports such as silica gel or alumina.

The names for the compounds of the present invention are generated using Symyx Version 3.1.NET with the IUPAC naming functionality.

Abbreviations used herein are defined as follows: "Brine" means a saturated aqueous sodium chloride solution; "BSA" means bovine serum albumin; "DDQ" means 2,3 dichloro-5,6-dicyano-1,4 benzoquinone; "EDTA" means ethylenediaminetetraacetic acid; "GDP" means guanosine diphosphate; "HEPES" means 4-(2-hydroxyethyl)-1-piperazineethanesulfonic acid; "MCPBA" means meta-chloroperoxybenzoic acid; "MeOH" means methanol; "THF" means tetrahydrofuran; "tBOC" means tert-butoxy carbonyl.

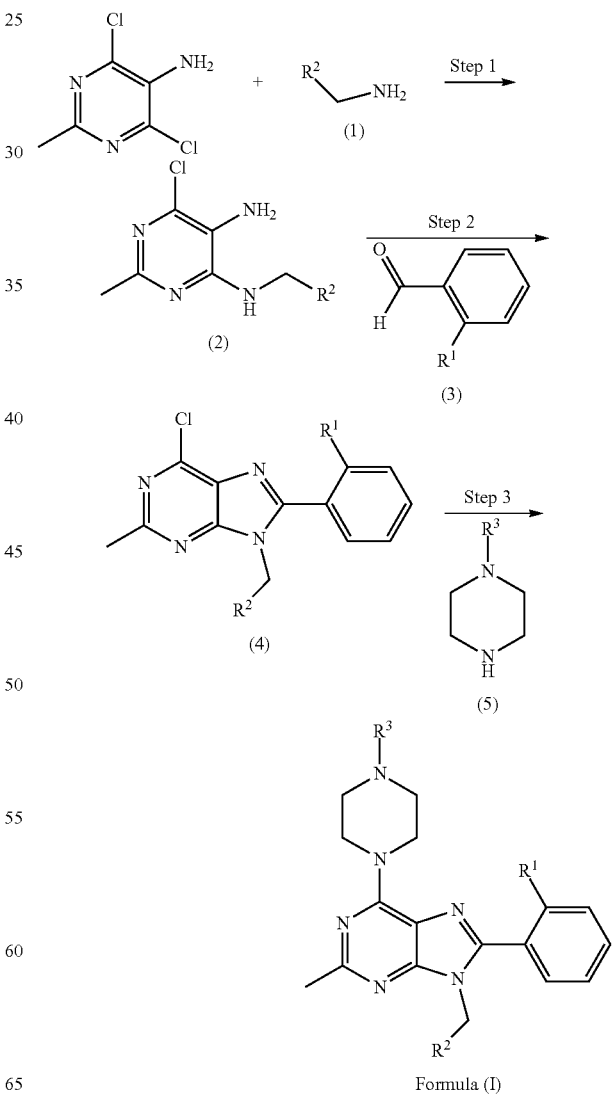

A compound of Formula (I) can be prepared in accordance with reactions as depicted in Scheme 1.

In Step 1, 4,6-dichloro-2-methyl-pyrimidin-5-ylamine is reacted with an amine (1) in a displacement reaction to provide a diamino pyrimidine (2). The reaction can proceed in the presence of a suitable base, such as triethylamine or diisopropylethylamine, in a solvent such as ethanol or isopropanol, at an elevated temperature such as about 90 to 160° C., preferably in a sealed tube. Alternatively the reaction can be accomplished using microwave irradiation.

In Step 2, an imine is formed from the diamino pyrimidine (2) and a benzaldehdye (3) in the presence of an acid catalyst such as ferric chloride on silica, or p-toluenesulfonic acid. The reaction takes place in a suitable solvent such as 1,4-dioxane or toluene, at an elevated temperature such as about 70° C. to 110° C. In the absence of silica, molecular sieves can be added to remove water from the reaction. After filtration to remove the solids and concentration, the oxidative cyclization of the imine can be accomplished in a suitable solvent such as dichloromethane, in the presence of an oxidate such as DDQ, at a suitable temperature such as about −30 to 40° C. to give a 6-chloropurine (4).

In Step 3, a 6-chloropurine (4) undergoes a displacement reaction with a piperazine (5) to provide a compound of Formula (I). The reaction can proceed in the presence of a suitable base, such as triethylamine or diisopropylethylamine, in a solvent such as methanol, ethanol, or isopropanol, at an elevated temperature such as about 50 to 100° C. Alternatively the reaction can be accomplished using microwave irradiation.

It will be recognized by one skilled in the art that the amine functionality present in the piperazinyl moiety, can be protected with a suitable protecting group such as tBOC. After the displacement in Step 3, the protecting group can be subsequently removed and the amine acylated or alkylated to make further compounds of Formula (I). Likewise, when $R^2$ includes amine functionality, the amine can be protected with a suitable protecting group such as a tBOC group in the afore mentioned sequences. It can subsequently be deprotected and acylated or sulfonylated to make additional compounds of the invention.

In addition some functional groups can undergo additional reactions at various steps in the synthetic route. For example, an acetamide intermediate (wherein $R^2=C(O)NH_2$) can be converted to a nitrile with phosphoryl chloride.

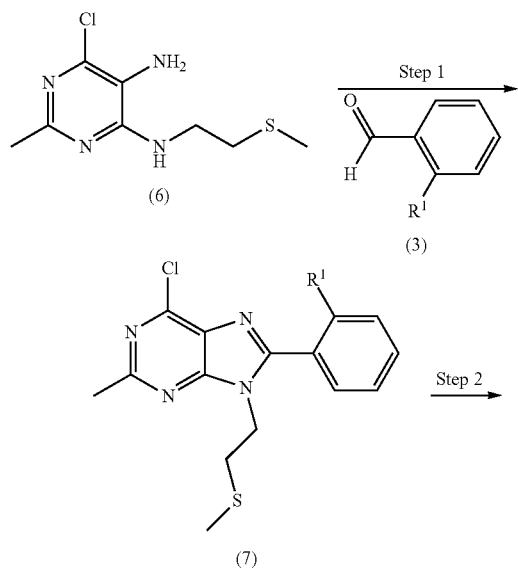

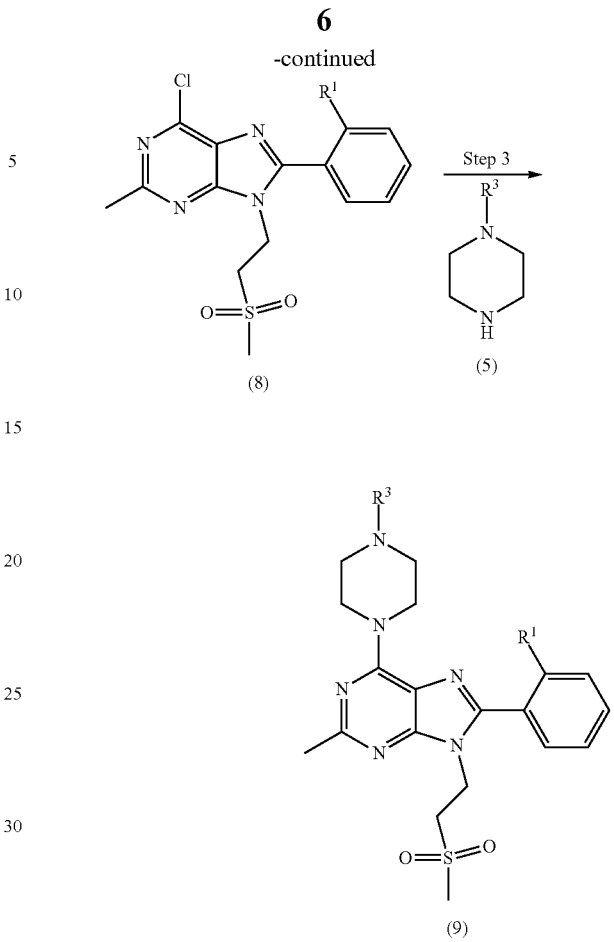

In Scheme 2 are depicted methods for making a compound of formula (9).

In Step 1, 6-chloro-2-methyl-N4-(2-methylsulfanylethyl)pyrimidine-4,5-diamine (6) is reacted with a benzaldehyde (3) essentially as described for Scheme 1, Step 2, above to provide an alkylthio purine (7)

In Step 2, an alkylthio purine (7) is oxidized to an alkylsulfonyl purine (8). The reaction proceeds in the presence of a suitable oxidizing agent such as MCPBA in a suitable solvent such as dichloromethane, at a suitable temperature such as about 0 to 40° C.

In Step 3, a chloro alkylsulfonyl purine (8) undergoes a displacement reaction with an appropriately substituted piperazine (5) to provide a piperazinyl purine (9) essentially as described in Scheme 1, Step 3, above.

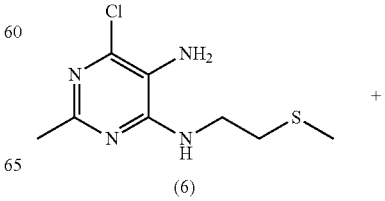

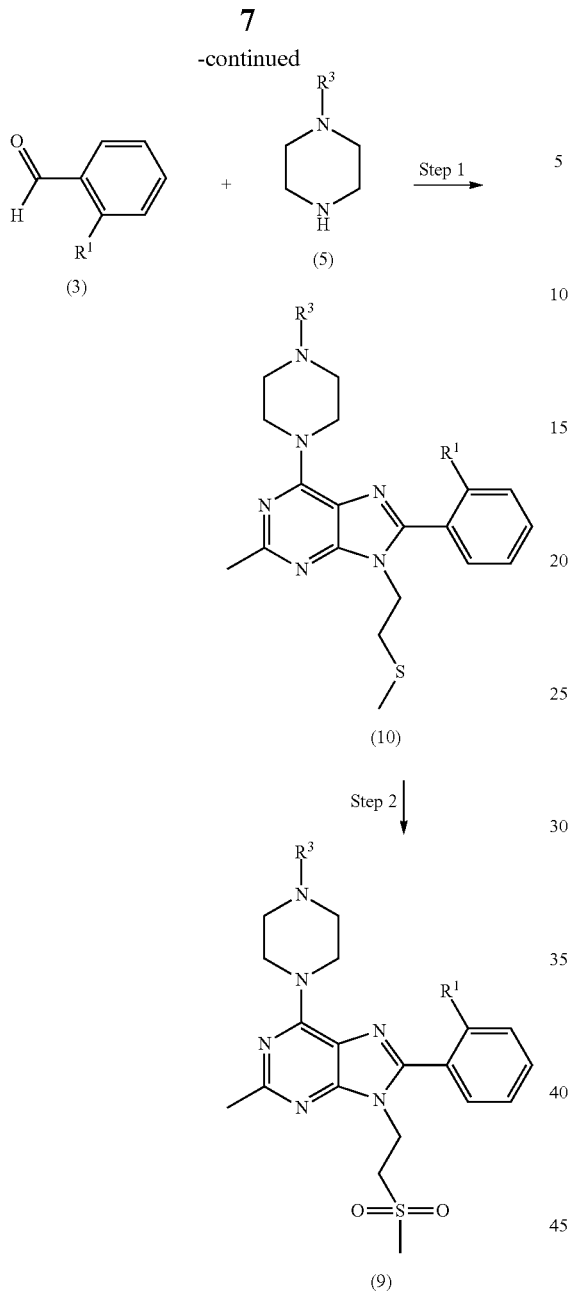

In Scheme 3 is depicted an alternative route to synthesizing compounds of formula (9).

In Step 1, 6-chloro-2-methyl-N4-(2-methylsulfanylethyl)pyrimidine-4,5-diamine (6) is combined together with a benzaldehyde (3) and a piperazine (5) in a suitable solvent, such as anisole, at an elevated temperature such as about 120 to 150° C., for a period of about 3 to 6 days, to provide an alkylthio piperazinyl purine (10).

In Step 2, an alkyl thio piperazinyl purine (10) is oxidized to the sulfone of formula (9). The reaction takes place in suitable solvent, for example, a mixture of THF and MeOH, using an aqueous solution of potassium peroxymonosulfate (Oxone®) at a suitable temperature such as about 0 to 60° C. Alternatively the alkylthio can be oxidized using MCPBA.

PREPARATION 1

6-Chloro-2-methyl-N4-(2-methylsulfanylethyl)pyrimidine-4,5-diamine

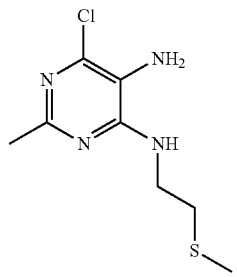

Heat a solution of 4,6-dichloro-2-methyl-pyrimidin-5-amine (46.0 g, 0.258 mol), 2-(methylthio)ethyl amine (40.05 g, 0.439 mol) and triethylamine (53.3 g, 0.517 mol) in isopropanol (500 mL) at 90° C. for 30 h. Cool the reaction mixture to room temperature and concentrate. Dissolve the residue in dichloromethane (2 L) and wash with water (2×500 mL) and brine (500 mL). Dry the organic layer over solid sodium sulfate, filter, and evaporate to afford a brown solid. Purify the residue on a silica gel column eluting with ethyl acetate to give the title compound (56 g). ES/MS (m/z) 233 (M+1).

Prepare the diamino pyrimidines in the table below by essentially following the procedure as described in Preparation 1, using the appropriate amine and 4,6-dichloro-2-methyl-pyrimidin-5-amine. Purify using silica gel chromatography with an eluent of dichloromethane/methanol, ethyl acetate/hexane (Preparation 6), or acetone/hexanes (Preparation 8).

| Prep | Chemical name | Structure | ES/MS m/z |
|---|---|---|---|
| 2 | 2-[(5-Amino-6-chloro-2-methyl-pyrimidin-4-yl)amino]acetamide | (structure) | 216 (M + 1) |

-continued
| Prep | Chemical name | Structure | ES/MS m/z |
|---|---|---|---|
| 3 | 3-[(5-Amino-6-chloro-2-methyl-pyrimidin-4-yl)amino]propanenitrile | 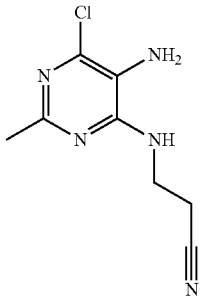 | 212 (M + 1) |
| 4 | tert-Butyl N-[2-[(5-amino-6-chloro-2-methyl-pyrimidin-4-yl)amino]ethyl]carbamate | 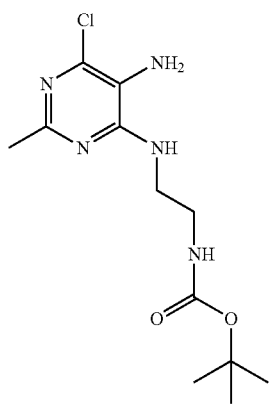 [SMILES: Cc1nc(Cl)c(N)c(NCCNC(=O)OC(C)(C)C)n1] | 302 (M + 1) |
| 5 | N-[2-[(5-Amino-6-chloro-2-methyl-pyrimidin-4-yl)amino]ethyl]acetamide | 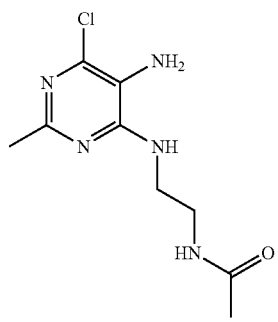 [SMILES: CC(=O)NCCNc1nc(C)nc(Cl)c1N] | 244 (M + 1) |
| 6 | 2-[(5-Amino-6-chloro-2-methyl-pyrimidin-4-yl)amino]-N-methyl-acetamide | 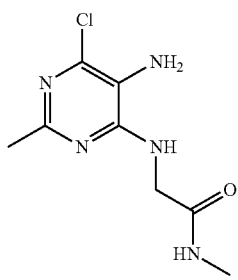 | 230 (M + 1) |

| Prep | Chemical name | Structure | ES/MS m/z |
|---|---|---|---|
| 7 | 1-[2-[(5-Amino-6-chloro-2-methyl-pyrimidin-4-yl)amino]ethyl]pyrrolidin-2-one | 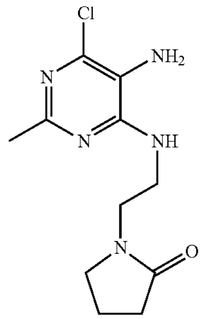 [SMILES: Cc1nc(Cl)c(N)c(NCCN2CCCC2=O)n1] | 270 (M + 1) |
| 8 | 6-Chloro-2-methyl-N4-(2-methylsulfonylethyl)pyrimidine-4,5-diamine | 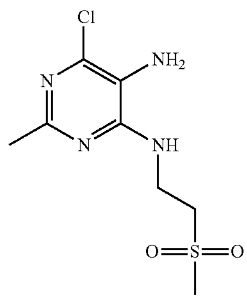 [SMILES: Cc1nc(Cl)c(N)c(NCCS(C)(=O)=O)n1] | 265 (M + 1) |

PREPARATION 9

6-Chloro-8-(2-chlorophenyl)-2-methyl-9-(2-methyl-sulfanylethyl)purine

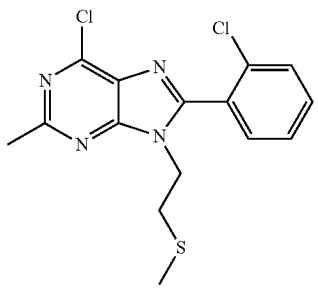 [SMILES: CSCCn1c(-c2ccccc2Cl)nc2c(Cl)nc(C)nc21]

Heat a mixture of 6-chloro-2-methyl-N4-(2-methylsulfanylethyl)pyrimidine-4,5-diamine (1.63 g, 0.007 mol), 2-chlorobenzaldehyde (1.96 g, 0.014 mol), and 15% FeCl$_3$ on SiO$_2$ (4.89 g) in 1,4-dioxane (15 mL) to 100° C. for 16 h. Cool the reaction and remove the silica by filtration through diatomaceous earth. Concentrate the filtrate under reduced pressure to give a residue. Dissolve the residue in dry dichloromethane (10 mL) and add 2,3-dichloro-5,6-dicyano-1,4-benzoquinone (1.58 g, 0.007 mol) at 0° C. Stir the reaction mixture at room temperature for 2 h. Dilute the reaction mixture with dichloromethane, and wash with 1 N aqueous sodium hydroxide solution, water and brine. Dry the organic layer over anhydrous sodium sulfate, filter, and concentrate to give a residue. Purify the residue on a silica gel column eluting with ethyl acetate:hexane (15:85) to give the title compound (1.9 g). ES/MS m/z 353 (M+1).

Prepare the phenylpurines in the table below by essentially following the procedure as described in Preparation 9, using the appropriate diamino pyrimidine and appropriate benzaldehyde. Purify by silica gel chromatography with an eluent of ethyl acetate:hexane, dichloromethane:methanol, or hexane:acetone.

| Prep | Chemical name | Structure | ES/MS m/z |
|---|---|---|---|
| 10 | 3-[6-Chloro-8-(2-chlorophenyl)-2-methyl-purin-9-yl]propanenitrile | 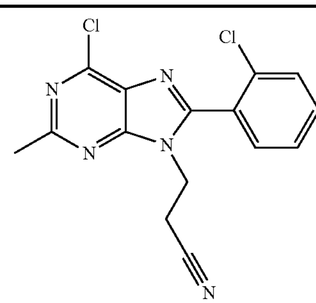 | 332 (M + 1) |

-continued

| Prep | Chemical name | Structure | ES/MS m/z |
|---|---|---|---|
| 11 | N-[2-[6-Chloro-8-(2-chlorophenyl)-2-methyl-purin-9-yl]ethyl]acetamide | 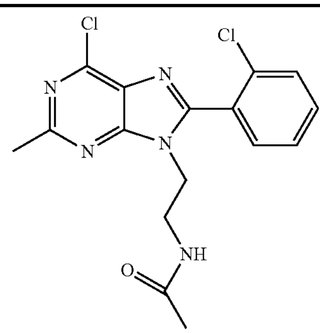 | 364 (M + 1) |
| 12 | 1-[2-[6-Chloro-8-(2-chlorophenyl)-2-methyl-purin-9-yl]ethyl]pyrrolidin-2-one | 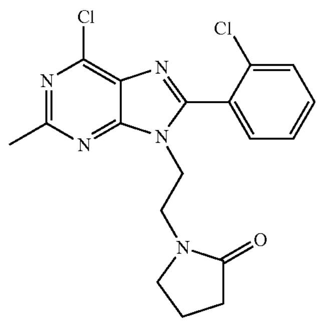 [SMILES: Cc1nc(Cl)c2nc(-c3ccccc3Cl)n(CCN3CCCC3=O)c2n1] | 390 (M + 1) |
| 13 | 2-[6-Chloro-8-(2-chlorophenyl)-2-methyl-purin-9-yl]-N-methyl-acetamide | 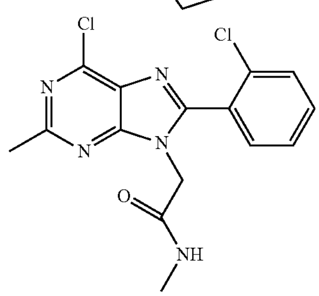 | 350 (M + 1) |
| 14 | 6-chloro-2-methyl-9-(2-methylsulfonylethyl)-8-(o-tolyl)purine | 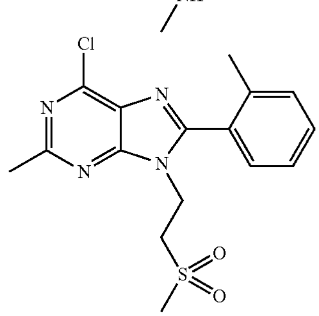 | 365 (M + 1) |

PREPARATION 15

2-[6-Chloro-8-(2-chlorophenyl)-2-methyl-purin-9-yl]acetamide

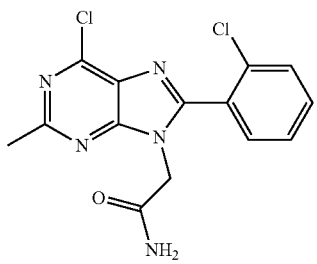 [SMILES: Cc1nc(Cl)c2nc(-c3ccccc3Cl)n(CC(N)=O)c2n1]

Heat a mixture of 2-[(5-amino-6-chloro-2-methyl-pyrimidin-4-yl)amino]acetamide (2.2 g, 0.01 mol), 2-chlorobenzaldehyde (2.86 g, 0.02 mol), p-toluene sulfonic acid (0.2 g) and molecular sieves (1.0 g) in toluene (50 mL) to reflux for 16 h. Cool and remove the sieves by filtration through diatomaceous earth. Concentrate the filtrate under reduced pressure to afford a residue. Dissolve the residue in dry dichloromethane (50 mL) and add 2,3-dichloro-5,6-dicyano-1,4-benzoquinone (2.3 g, 0.01 mol) at 0° C. Allow to warm to room temperature and stir for 2 h. Dilute the reaction mixture with dichloromethane, wash with 1 N aqueous sodium hydroxide solution, water, and brine. Dry the organic layer over anhydrous sodium sulfate, filter, and concentrate to give a residue. Purify the residue on a silica gel column eluting with dichloromethane:methanol (98:2) to provide the title compound (0.3 g). ES/MS m/z 336 (M+1).

Prepare the phenylpurine in the table below by essentially following the procedure as described in Preparation 15, using the appropriate diamino pyrimidine and 2-chlorobenzaldehyde.

| Prep | Chemical name | Structure | ES/MS m/z |
|---|---|---|---|
| 16 | tert-Butyl N-[2-[6-chloro-8-(2-chlorophenyl)-2-methyl-purin-9-yl]ethyl]carbamate | 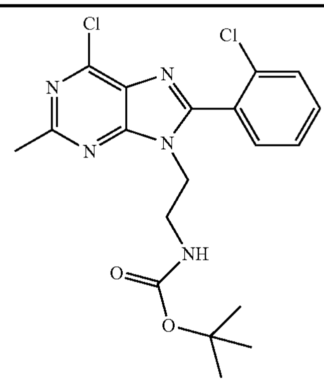 | 422 (M + 1) |

PREPARATION 17

2-[6-Chloro-8-(2-chlorophenyl)-2-methyl-purin-9-yl]acetonitrile

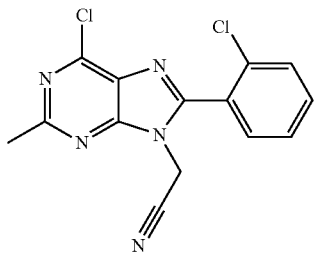 [SMILES: Cc1nc(Cl)c2nc(-c3ccccc3Cl)n(CC#N)c2n1]

Heat a solution of 2-[6-chloro-8-(2-chlorophenyl)-2-methyl-purin-9-yl]acetamide (0.3 g, 0.8 mmol) and phosphoryl chloride (2.5 mL) at 110° C. for 16 h. Quench the reaction with aqueous sodium bicarbonate solution and extract with dichloromethane. Wash the organics with water and brine. Dry the organic layer over anhydrous sodium sulfate, filter, and concentrate to give the title compound (0.2 g). ES/MS m/z 318 (M+1).

PREPARATION 18

6-Chloro-8-(2-chlorophenyl)-2-methyl-9-(2-methylsulfonylethyl)purine

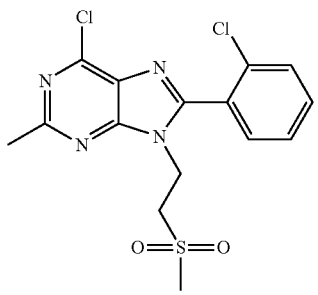 [SMILES: Cc1nc(Cl)c2nc(-c3ccccc3Cl)n(CCS(C)(=O)=O)c2n1]

Add meta-chloroperbenzoic acid (2.4 g, 0.014 mol) to a solution of 6-chloro-8-(2-chlorophenyl)-2-methyl-9-(2-methylsulfanylethyl)purine (1.98 g, 5.0 mmol) in dichloromethane (15 mL) and heat to reflux for 6 h. Cool the reaction mixture, quench with saturated sodium bicarbonate solution, and extract with ethyl acetate. Dry the organic layer over anhydrous sodium sulfate, filter, and concentrate under reduced pressure to give a residue. Purify the residue on a silica gel column eluting with dichloromethane:methanol (98:2) to afford the title compound (1.95 g). ES/MS m/z 385 (M+1).

PREPARATION 19

1-(2-Fluoroethyl)piperazine dihydrochloride

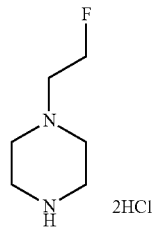

Charge a reaction vessel with N-tert-butoxycarbonylpiperazine (1.600 g, 8.590 mmol), potassium carbonate (3.56 g, 25.77 mmol), sodium iodide (catalytic) (10 mg, 66.7 µmol), 1,4-dioxane (20 mL), and 1-bromo-2-fluoroethane (704.0 µL 9.45 mmol). Heat the mixture with stirring at reflux temperature overnight. Upon reaction completion, cool to room temperature and concentrate under reduced pressure. Partition the resulting residue with ethyl acetate and water. Separate the organic layer and dry over anhydrous sodium sulfate, filter, and concentrate under reduced pressure to afford pure 4-(2-fluoro-ethyl)-piperazine-1-carboxylic acid tert-butyl ester. GC-MS m/z 232 (M).

Add 4 N HCl in 1,4-dioxane (21.52 mL, 86.1 mmol) to a stirred solution of 4-(2-fluoro-ethyl)-piperazine-1-carboxylic acid tert-butyl ester (2.00 g, 8.61 mmol) in dry dichloromethane (60 mL) at room temperature under nitrogen. Stir overnight under nitrogen. Concentrate the reaction under reduced pressure to afford the title compound (1.78 g). ES/MS m/z 133 (M+1).

EXAMPLE 1

8-(2-Chlorophenyl)-6-(4-methylpiperazin-1-yl)-2-methyl-9-(2-methylsulfonylethyl)purine hydrochloride

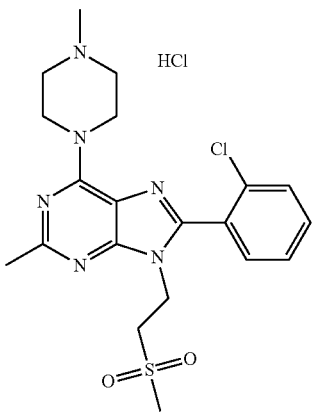 [SMILES: Cc1nc(N2CCN(C)CC2)c2nc(-c3ccccc3Cl)n(CCS(C)(=O)=O)c2n1 ; Cl]

Heat a solution of 6-chloro-8-(2-chlorophenyl)-2-methyl-9-(2-methylsulfonylethyl)purine (0.3 g, 0.0007 mol), N-methylpiperazine (0.08 g, 0.0008 mol) and triethylamine (0.08 g, 0.0008 mol) in ethanol (15 mL) at 90° C. for 16 h. Cool and concentrate the reaction mixture under reduced pressure. Dissolve the residue in dry dichloromethane and wash with saturated sodium bicarbonate solution, water, and brine. Dry the organic layer over anhydrous sodium sulfate, filter, and concentrate to give a residue. Purify the residue on a silica gel column using dichloromethane:methanol (96:4) as eluent to afford a 8-(2-chlorophenyl)-6-(4-methylpiperazin-1-yl)-2-methyl-9-(2-methylsulfonylethyl)purine (0.24 g). ES/MS m/z 449 (M+1).

Add HCl (2.0 M solution in ether) (0.018 g, 0.0005 mol, 1.0 eq) to a solution of 8-(2-chlorophenyl)-2-methyl-6-(4-methylpiperazin-1-yl)-9-(2-(methylsulfonyl)ethyl)-9H-purine (0.24 g, 0.0005 mol) in ether (4 mL) at 0° C. and stir for 2 h at room temperature. Filter the precipitate and wash with ether and dry under vacuum to provide the title compound (0.15 g) as white solid. ES/MS m/z 449 (M+1).

Prepare the phenyl piperazinylpurines in the table below by essentially following the procedure as described in Example 1, using the appropriately substituted piperazine and substituted 6-chloropurine.

| Ex or Prep | Chemical name | Structure | ES/MS m/z |
|---|---|---|---|
| Ex 2 | 8-(2-Chlorophenyl)-6-(4-ethylpiperazin-1-yl)-2-methyl-9-(2-methylsulfonylethyl)purine hydrochloride | 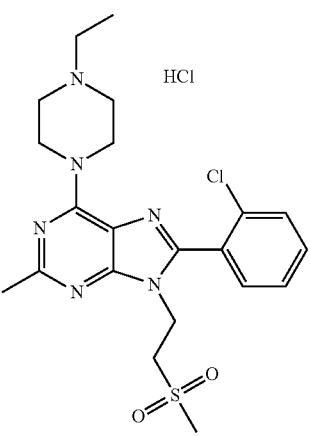 [SMILES: CCN1CCN(c2nc(C)nc3c2nc(-c2ccccc2Cl)n3CCS(C)(=O)=O)CC1 ; Cl] | 463 (M + 1) |
| Ex 3 | 2-[8-(2-Chlorophenyl)-2-methyl-6-(4-methylpiperazin-1-yl)purin-9-yl]acetonitrile hydrochloride | 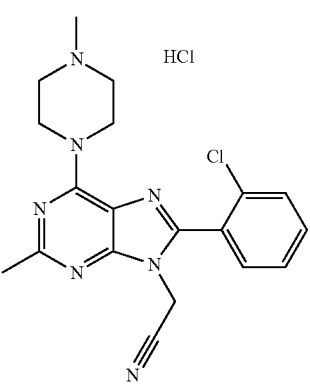 [SMILES: Cc1nc(N2CCN(C)CC2)c2nc(-c3ccccc3Cl)n(CC#N)c2n1 ; Cl] | 382 (M + 1) |

-continued
| Ex or Prep | Chemical name | Structure | ES/MS m/z |
|---|---|---|---|
| Ex 4 | 3-[8-(2-Chlorophenyl)-2-methyl-6-(4-methylpiperazin-1-yl)purin-9-yl]propanenitrile hydrochloride | 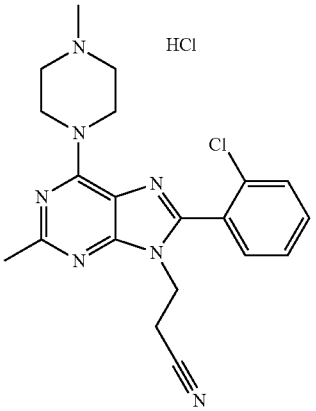 [SMILES: Cc1nc(N2CCN(C)CC2)c2nc(-c3ccccc3Cl)n(CCC#N)c2n1 ; Cl] | 396 (M + 1) |
| Ex 5 | 2-Methyl-6-(4-methylpiperazin-1-yl)-9-(2-methylsulfonylethyl)-8-(o-tolyl)purine hydrochloride | 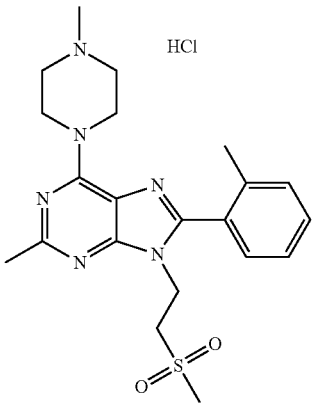 [SMILES: Cc1nc(N2CCN(C)CC2)c2nc(-c3ccccc3C)n(CCS(C)(=O)=O)c2n1 ; Cl] | 429 (M + 1) |
| Ex 6 | N-[2-[8-(2-Chlorophenyl)-2-methyl-6-(4-methylpiperazin-1-yl)purin-9-yl]ethyl]acetamide hydrochloride | 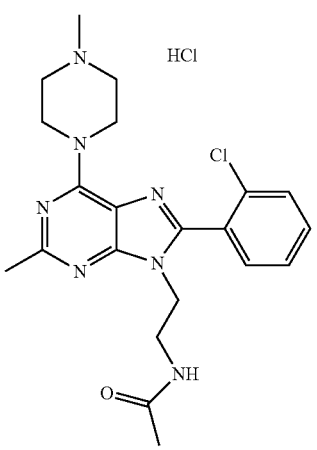 [SMILES: CC(=O)NCCn1c(-c2ccccc2Cl)nc2c(N3CCN(C)CC3)nc(C)nc21 ; Cl] | 428 (M + 1) |

-continued
| Ex or Prep | Chemical name | Structure | ES/MS m/z |
|---|---|---|---|
| Ex 7 | N-[2-[8-(2-Chlorophenyl)-6-(4-ethylpiperazin-1-yl)-2-methyl-purin-9-yl]ethyl]acetamide hydrochloride | 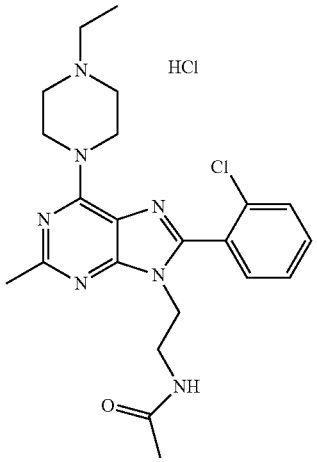 [SMILES: CCN1CCN(c2nc(C)nc3c2nc(-c2ccccc2Cl)n3CCNC(C)=O)CC1 ; Cl] | 442 (M + 1) |
| Ex 8 | 1-[4-[8-(2-Chlorophenyl)-2-methyl-9-(2-methylsulfonylethyl)purin-6-yl]piperazin-1-yl]ethanone hydrochloride | 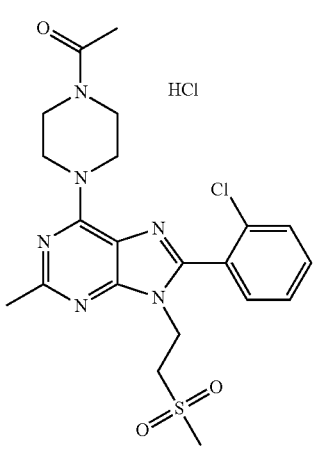 [SMILES: CC(=O)N1CCN(c2nc(C)nc3c2nc(-c2ccccc2Cl)n3CCS(C)(=O)=O)CC1 ; Cl] | 477 (M + 1) |
| Ex 9 | 2-[8-(2-Chlorophenyl)-6-(4-ethylpiperazin-1-yl)-2-methyl-purin-9-yl]-N-methyl-acetamide hydrochloride | 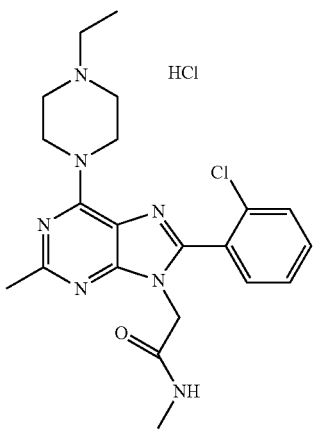 [SMILES: CCN1CCN(c2nc(C)nc3c2nc(-c2ccccc2Cl)n3CC(=O)NC)CC1 ; Cl] | 428 (M + 1) |

-continued
| Ex or Prep | Chemical name | Structure | ES/MS m/z |
|---|---|---|---|
| Ex 10 | 1-[2-[8-(2-Chlorophenyl)-2-methyl-6-(4-methylpiperazin-1-yl)purin-9-yl]ethyl]pyrrolidin-2-one hydrochloride | 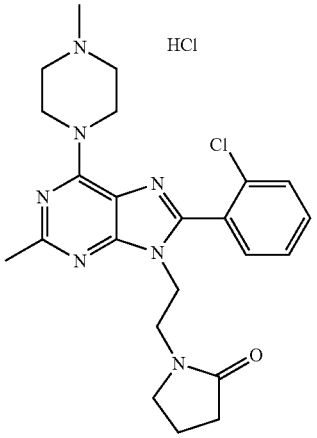 [SMILES: Cc1nc(N2CCN(C)CC2)c2nc(-c3ccccc3Cl)n(CCN3CCCC3=O)c2n1 ; Cl] | 454 (M + 1) |
| Prep 20 | tert-Butyl N-[2-[8-(2-chlorophenyl)-6-(4-ethylpiperazin-1-yl)-2-methyl-purin-9-yl]ethyl]carbamate | 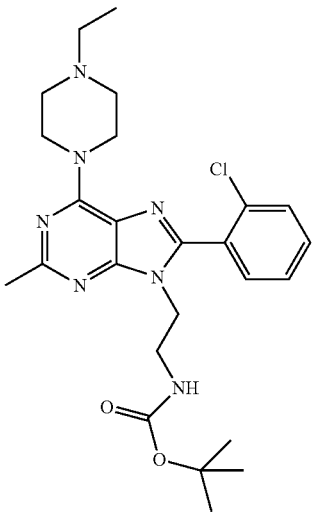 [SMILES: CCN1CCN(c2nc(C)nc3c2nc(-c2ccccc2Cl)n3CCNC(=O)OC(C)(C)C)CC1] | 500 (M + 1) |
| Prep 21 | tert-Butyl N-[2-[8-(2-chlorophenyl)-6-[4-(2-fluoroethyl)piperazin-1-yl]-2-methyl-purin-9-yl]ethyl]carbamate | 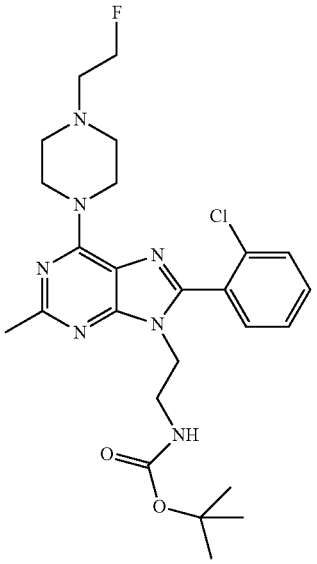 [SMILES: Cc1nc(N2CCN(CCF)CC2)c2nc(-c3ccccc3Cl)n(CCNC(=O)OC(C)(C)C)c2n1] | 518 (M + 1) |

| Ex or Prep | Chemical name | Structure | ES/MS m/z |
|---|---|---|---|
| Prep 22 | tert-Butyl N-[2-[8-(2-chlorophenyl)-2-methyl-6-(4-methylpiperazin-1-yl)purin-9-yl]ethyl]carbamate | 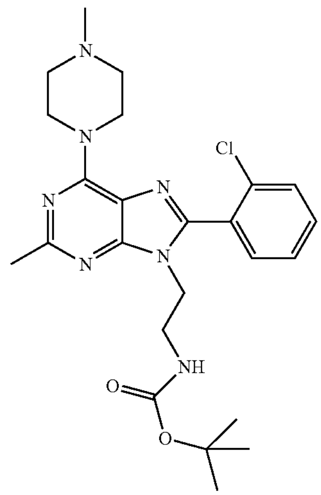 [SMILES: Cc1nc(N2CCN(C)CC2)c2nc(-c3ccccc3Cl)n(CCNC(=O)OC(C)(C)C)c2n1] | 486 (M + 1) |
| Prep 23 | tert-Butyl N-[2-[6-(4-acetylpiperazin-1-yl)-8-(2-chlorophenyl)-2-methyl-purin-9-yl]ethyl]carbamate | 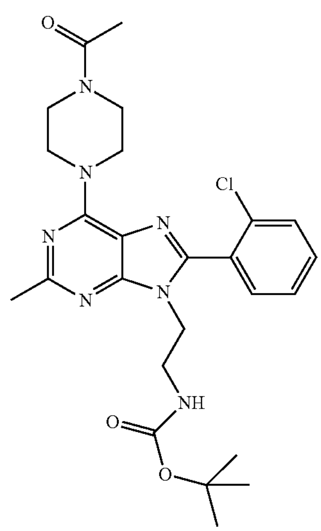 [SMILES: CC(=O)N1CCN(c2nc(C)nc3c2nc(-c2ccccc2Cl)n3CCNC(=O)OC(C)(C)C)CC1] | 514 (M + 1) |

PREPARATION 24

8-(2-Chlorophenyl)-2-methyl-6-(4-methylpiperazin-1-yl)-9-(2-methylsulfanylethyl)purine

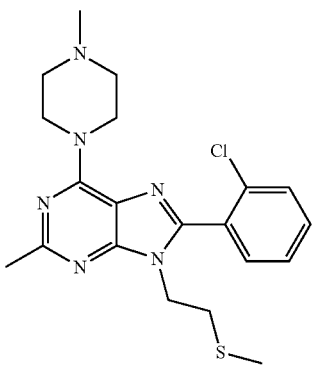 [SMILES: CSCCn1c(-c2ccccc2Cl)nc2c(N3CCN(C)CC3)nc(C)nc21]

Dissolve 6-chloro-2-methyl-N4-(2-(methylthio)ethyl)pyrimidine-4,5-diamine (28.1 g, 120.7 mmol), and N-methyl piperazine (14.76 ml, 132.81 mmol) in methoxybenzene in a 2 L round bottom flask. Add 2-chlorobenzaldehyde (20.38 mL, 181.1 mmol) in one portion and raise the temperature to 140° C. and maintain at this temperature for 4 days. Cool the reaction mixture and concentrate under reduced pressure. Dilute the resulting oil with 2 N aqueous hydrogen chloride (200 mL) and wash with dichloromethane (500 mL). Discard the organic layer. Treat the aqueous layer with a sodium hydroxide solution until pH=14 is attained. Extract into dichloromethane. Dry the organics over anhydrous sodium sulfate, filter, and concentrate to give the title compound as a brown oil (43 g). ES/MS m/z 417 (M+1).

EXAMPLE 11

8-(2-Chlorophenyl)-2-methyl-6-(4-methylpiperazin-1-yl)-9-(2-methylsulfonylethyl)purine hydrochloride

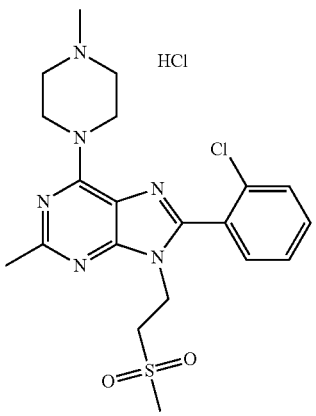 [SMILES: Cc1nc(N2CCN(C)CC2)c2nc(-c3ccccc3Cl)n(CCS(C)(=O)=O)c2n1 ; Cl]

Dissolve 8-(2-chlorophenyl)-2-methyl-6-(4-methylpiperazin-1-yl)-9-(2-methylsulfanylethyl)purine (38.5 g, 92.3 mmol) in a solution of tetrahydrofuran (277 mL) and methanol (277 mL). Prepare a solution of potassium peroxymonosulfate (Oxone®) (79.5 g, 129.3 mmol) in water (554 mL). Add the potassium peroxymonosulfate solution (300 mL) over a 5 min period and stir for 30 min. Then add additional potassium peroxymonosulfate solution (150 mL, followed by 50 mL after 30 min). Stir the reaction mixture for 30 min following the final addition. Add solid sodium metabisulfite (49.1 g, 258.5 mmol) and stir the mixture at ambient temperature overnight. Add aqueous sodium bicarbonate solution (400 mL) and extract into ethyl acetate (3×1 L). Dry the combined organic layer over anhydrous sodium sulfate, filter, and concentrate to afford an orange residue. Purify the residue on a silica gel column using 5-50% ethanol in 1:1 dichloromethane-hexane as eluent. Combine and evaporate the appropriate fractions to provide a solid. Triturate the solid with ether and dry under vacuum to afford 8-(2-chlorophenyl)-2-methyl-6-(4-methylpiperazin-1-yl)-9-(2-methylsulfonylethyl)purine (11.4 g). ES/MS m/z 449 (M+1).

Suspend 8-(2-chlorophenyl)-2-methyl-6-(4-methylpiperazin-1-yl)-9-(2-methylsulfonylethyl)purine (11.3 g, 25.2 mmol) in ethanol (150 mL) and add 1 N aqueous hydrogen chloride solution (6.29 mL, 25.2 mmol, 1 eq). Allow the mixture to stir overnight and concentrate under reduced pressure. Collect the precipitated solids by filtration, wash with acetone, and dry under vacuum to afford the title compound (10.6 g). ES/MS m/z 449 (M+1).

EXAMPLE 12

2-[8-(2-Chlorophenyl)-6-(4-ethylpiperazin-1-yl)-2-methyl-purin-9-yl]ethanamine hydrochloride

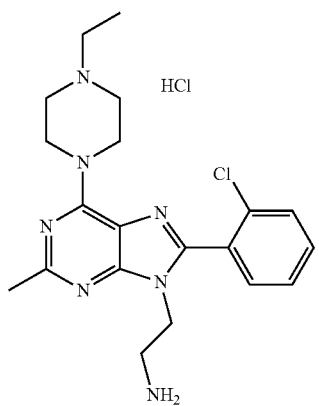 [SMILES: CCN1CCN(c2nc(C)nc3c2nc(-c2ccccc2Cl)n3CCN)CC1 ; Cl]

Add trifluoroacetic acid (3 mL) to a solution of tert-butyl N-[2-[8-(2-chlorophenyl)-6-(4-ethylpiperazin-1-yl)-2-methyl-purin-9-yl]ethyl]carbamate (0.6 g, 1.2 mmol) in dichloromethane (3 mL) at 0° C. and stir for 2 h at room temperature. Quench the reaction mixture with saturated aqueous sodium bicarbonate solution, and extract with dichloromethane. Dry the organic layer over anhydrous sodium sulfate, filter, and concentrate to give a residue. Purify the residue on a silica gel column using dichloromethane-methanol (96:4) as eluent to give 2-[8-(2-chlorophenyl)-6-(4-ethylpiperazin-1-yl)-2-methyl-purin-9-yl]ethanamine (0.3 g). ES/MS m/z 400 (M+1).

Add HCl (2.0 M solution in ether) (0.027 g, 0.7 mmol) to a mixture of 2-[8-(2-chlorophenyl)-6-(4-ethylpiperazin-1-yl)-2-methyl-purin-9-yl]ethanamine (0.3 g, 0.7 mmol) in ether (5 mL) at 0° C. and stir for 2 h at room temperature. Collect the precipitate by filtration and wash with ether. Dry under vacuum to give the title compound (0.25 g) as a white solid. ES/MS m/z 400 (M+1).

EXAMPLE 13

Methyl N-[2-[8-(2-chlorophenyl)-2-methyl-6-(4-methylpiperazin-1-yl)purin-9-yl]ethyl]carbamate hydrochloride

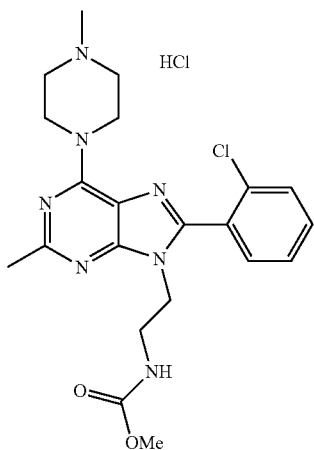 [SMILES: COC(=O)NCCn1c(-c2ccccc2Cl)nc2c(N3CCN(C)CC3)nc(C)nc21 ; Cl]

Add trifluoroacetic acid (5 mL) to a solution of tert-butyl N-[2-[8-(2-chlorophenyl)-2-methyl-6-(4-methylpiperazin-1-yl)purin-9-yl]ethyl]carbamate (0.51 g, 0.001 mol) in dichloromethane (5 mL) at 0° C. Allow the reaction to warm to room temperature and stir for 2 h. Quench the reaction mixture with saturated aqueous sodium bicarbonate solution and then extract with dichloromethane. Dry the organic layer over anhydrous sodium sulfate, filter, and concentrate to give 2-[8-(2-chlorophenyl)-2-methyl-6-(4-methylpiperazin-1-yl)purin-9-yl]ethanamine (0.39 g). ES/MS m/z 386 (M+1).

Add methyl chloroformate (0.25 g, 0.0027 mol) to a solution of 2-[8-(2-chlorophenyl)-2-methyl-6-(4-methylpiperazin-1-yl)purin-9-yl]ethanamine (0.39 g, 0.0010 mol) and pyridine (4.0 mL) in dry dichloromethane (4 mL) at 0° C. Allow to warm to room temperature and stir for 2 hour. Quench the reaction mixture with saturated aqueous sodium bicarbonate solution and then extract with dichloromethane. Dry the organic layer over anhydrous sodium sulfate, filter, and concentrate to give a residue. Purify the residue on a silica gel column using dichloromethane:methanol (97:3) as eluent to afford methyl N-[2-[8-(2-chlorophenyl)-2-methyl-6-(4-methylpiperazin-1-yl)purin-9-yl]ethyl]carbamate (0.3 g). ES/MS m/z 444 (M+1).

Add HCl (2.0 M solution in ether) (0.024 g, 0.0006 mol) to a solution of methyl N-[2-[8-(2-chlorophenyl)-2-methyl-6-(4-methylpiperazin-1-yl)purin-9-yl]ethyl]carbamate (0.3 g, 0.0006 mol) in ether (6 mL) at 0° C. and stir for 2 h at room temperature. Filter the precipitate, wash with ether, and dry under vacuum to afford the title compound (0.28 g) as a white solid. ES/MS m/z 444 (M+1).

Prepare the Examples in the table below by essentially following the procedures as described in Example 13, starting with tert-butyl N-[2-[8-(2-chlorophenyl)-6-[4-(2-fluoroethyl)piperazin-1-yl]-2-methyl-purin-9-yl]ethyl]carbamate or tert-butyl N-[2-[6-(4-acetylpiperazin-1-yl)-8-(2-chlorophenyl)-2-methyl-purin-9-yl]ethyl]carbamate. Deprotect and react with methyl chloroformate, methanesulfonyl chloride, or acetic anhydride.

| Ex | Chemical name | Structure | ES/MS m/z |
|---|---|---|---|
| 14 | Methyl N-[2-[6-(4-acetylpiperazin-1-yl)-8-(2-chlorophenyl)-2-methyl-purin-9-yl]ethyl]carbamate hydrochloride | 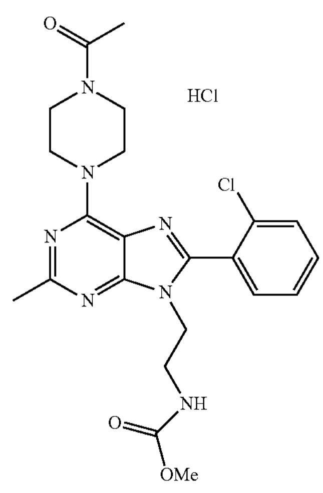 [SMILES: COC(=O)NCCn1c(-c2ccccc2Cl)nc2c(N3CCN(C(C)=O)CC3)nc(C)nc21 ; Cl] | 472 (M + 1) |

-continued

| Ex | Chemical name | Structure | ES/MS m/z |
|---|---|---|---|
| 15 | N-[2-[8-(2-Chlorophenyl)-6-[4-(2-fluoroethyl)piperazin-1-yl]-2-methyl-purin-9-yl]ethyl]methanesulfonamide hydrochloride | 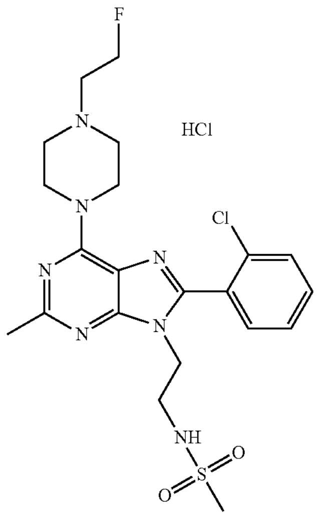 [SMILES: Cc1nc(N2CCN(CCF)CC2)c2nc(-c3ccccc3Cl)n(CCNS(C)(=O)=O)c2n1 ; Cl] | 496 (M + 1) |
| 16 | Methyl N-[2-[8-(2-chlorophenyl)-6-[4-(2-fluoroethyl)piperazin-1-yl]-2-methyl-purin-9-yl]ethyl]carbamate hydrochloride | 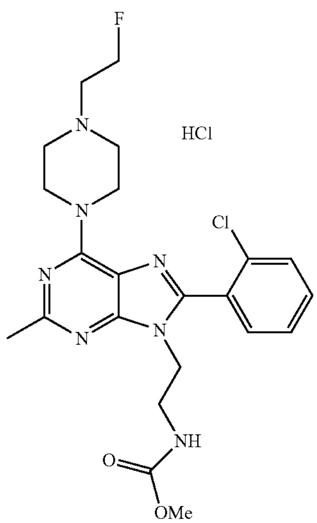 [SMILES: COC(=O)NCCn1c(-c2ccccc2Cl)nc2c(N3CCN(CCF)CC3)nc(C)nc21 ; Cl] | 476 (M + 1) |
| 17 | N-[2-[8-(2-chlorophenyl)-6-[4-(2-fluoroethyl)piperazin-1-yl]-2-methyl-purin-9-yl]ethyl]acetamide hydrochloride | 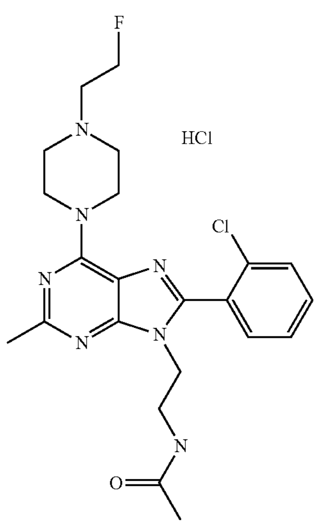 [SMILES: CC(=O)NCCn1c(-c2ccccc2Cl)nc2c(N3CCN(CCF)CC3)nc(C)nc21 ; Cl] | 460 (M + 1) |

CB$_1$ and CB$_2$ In Vitro Functional Assays

Exemplified compounds are tested in agonist mode using a SPA based GTP-γ-$^{35}$S binding assay. All assay components are prepared in assay buffer made up of 20 mM HEPES, 100 mM NaCl, 5 mM MgCl$_2$, (pH 7.4 at room temperature). Semi-log compound dilutions are done in assay buffer containing BSA (final 0.125%). GTP-γ$^{35}$-S binding is measured in a 96 well format using a whole membrane capture technique for the CB$_1$ assay and modifications of an antibody capture technique previously described (DeLapp et al. *J Pharmacol Exp Ther* 289:946-955, 1999) for the CB$_2$ assay. All incubations are done at room temperature.

CB$_1$:

hCB$_1$-CHO membranes, GDP (1 uM final), and saponin (10 ug/mL final) are added to assay buffer and homogenized. Diluted compounds, GTP-γ-$^{35}$S (500 nM final) and membranes are added to the assay plate and incubated for 30 minutes. Then 1 mg/well Wheatgerm Agglutinin SPA bead is added, and the plates are sealed, vortexed, and incubated for an additional hour. Plates are then centrifuged at 700×g for 10 minutes and counted for 1 minute per well using a scintillation counter.

CB$_2$-Sf9:

hCB$_2$-Sf9 membranes and GDP (1 uM final) are added to assay buffer and homogenized. Diluted compounds and membranes are added to the assay plate and pre-incubated for 15 minutes. This is followed by addition of GTP-γ-$^{35}$S (500 nM final) and another 35 minute incubation. Next a mixture containing Nonidet P40 detergent (0.2% final), anti-Gi antibody (final dilution of 1:362), and 1.25 mg anti-rabbit antibody scintillation proximity assay beads are added. The plates are then sealed, vortexed, and incubated for an additional 2 hours before centrifuging and counting as for CB$_1$.

To analyze data, first subtract background from all wells. Determine percent agonist efficacy by normalizing agonist/inverse agonist dose response data to a full agonist (methanandamide) response. Analyze the data using a 4-parameter logistic reduced fit with Activity Base and XLFit3.

All of the exemplified compounds were tested essentially as described above and each was found to have a relative EC50 value for CB$_2$ of ≤100 nM. Example 2 has a relative EC50 value for CB$_2$ of 17.2 nM and for CB$_1$ of 5560 nM. Example 16 has a relative EC50 value for CB$_2$ of 13.5 nM and for CB$_1$ of >100000 nM.

Thus, compounds of the present invention show CB$_2$ in vitro activity. Further, compounds of the present invention show selectivity for CB$_2$ over CB$_1$ and so provide limited potential for centrally mediated side effects.

Displacement of 3H-CP55940 from Human and Rat CB$_2$ Receptors

The methods of Felder et al. (*Mol. Pharmaocol.* 48:443-450, 1995) were utilized with minor modifications. Specifically, membrane homogenates from cells stably or transiently expressing the human or rat CB$_2$ receptor were washed by centrifugation and diluted into a 50 mM Tris HCl (pH 7.4), 5 mM MgCl$_2$, 2.5 mM EDTA, and 0.1% BSA buffer. Specific binding of 3H-CP55940 was defined with 1 μM CP55940. The ability of compounds to displace specific 3H-CP55940 binding was tested over a range of concentrations in the Tris, MgCl$_2$, EDTA, BSA buffer in the presence of 1% dimethyl sulfoxide by incubating at room temperature for 90 minutes in a volume of 300 μl. Unifilter 96-well microplates pretreated with 0.5% polyvinylpyrrolidone, 0.1% polysorbate 20 in water were washed three times with cold Tris buffer. The reaction mixture was then transferred to the filter plate immediately before terminating the incubation by rapid filtration and three 200 μl washes with cold Tris buffer. After the filter plates dried, microscint 20 was added to each well, the plate sealed and counted for determination of disintegrations per minute. The displacement curves were graphed and the resulting Ki values determined utilizing Graphpad Prism.

Example 3 has a human receptor Ki value of 27.8 nM and a rat receptor Ki value of 12.6 nM. Example 2 has a human receptor Ki value of 28.4 nM and a rat receptor Ki value of 48.7 nM.

Thus, compounds of the present invention are shown to bind to both human and rat CB$_2$ receptors in vitro.

Monoiodoacetate (MIA) Model

For all studies male Lewis rats of approximately 8 weeks of age at the time of MIA injection are used to measure pain in the MIA model. The rats are housed in groups of 2 or 3 per cage and maintained in a constant temperature and on a 12 hour light/12 hour dark cycle. Animals have free access to food and water at all times except during data collection.

In the standard MIA model the right knees of each rat are injected with 0.3 mg MIA in 50 ul of saline and the left knees with 50 ul of saline. Pain is measured at varying times after MIA injection (not normally before 10 day post MIA injection) using incapacitance testing. This measures the difference in hind paw weight bearing between the MIA and saline injected knees, and each measurement is the average of 3 separate measurements each measured over 1 second.

For studies with CB$_2$ agonists rats are randomized into dose groups (n=5 or 6) and then dosed once with the compound under investigation. Dosing is staggered by 15 minutes for each rat and at a predetermined time post-dose (usually 2 hours), pain measured using incapacitance testing. Studies are routinely run with 4 groups, vehicle (1% carboxy methyl cellulose in water plus 0.25% polysorbate 80) and 3 compound groups which can be either single compounds at a single dose or the same compound at 3 doses. Results are reported as the difference in weight bearing between saline and MIA injected knees and statistical comparisons are made between vehicle treated and compound treated animals to assess the effect of compounds on knee pain in the model.

Example 1 was tested essentially as described above and found to reduce pain versus vehicle at doses of 0.3 and 1 mg/kg. Example 17 was tested essentially as described above and found to reduce pain versus vehicle at doses of 0.1, 0.3 and 1 mg/kg.

Thus, compounds of the present invention are shown to be useful in the treatment of pain, in particular joint pain.

Animal Model of Dural Plasma Protein Extravasation (PPE)

Male Harlan Sprague-Dawley rats (250-350 g) are anesthetized with sodium pentobarbital (65 mg/kg, i.p.) and placed in a stereotaxic frame (David Kopf Instruments) with the incisor bar set at −2.5 mm. Following a midline sagital scalp incision, two pairs of bilateral holes are drilled through the skull (3.2 mm posteriorly, 1.8 and 3.8 mm laterally, all coordinates referenced to bregma). Pairs of stainless steel stimulating electrodes, insulated except at the tips (Rhodes Medical Systems, Inc.), are lowered through the holes in both hemispheres to a depth of 9.2 mm.

The femoral vein is exposed and a dose of the test compound is injected intravenously (i.v.) at a dosing volume of 1 mL/kg Approximately 8 minutes post i.v. injection, a 20 mg/kg dose of Fluorescein isothiocyanate-bovine serum albumin (FITC-BSA) is also injected intravenously. The FITC-BSA functions as a marker for protein extravasation. Ten minutes post-injection of the test compound, the left trigeminal ganglion is stimulated for 5 minutes at a current intensity of 1.0 mA (5 Hz, 5 msec duration) with a Model S48 Grass Instrument Stimulator with PSIU6 photoelectric isolation unit (Grass-Telefactor).

Alternatively, rats fasted overnight are dosed orally with test compound via gavage at a volume of 2 mL/kg. Approximately 50 minutes later the animals are anesthetized and placed in the stereotaxic frame as described above. 60 minutes post-p.o. dosing, the animals are dosed with FITC-BSA (20 mg/kg, i.v.). One hour post-p.o. dosing, the animals are stimulated as described above.

Five minutes following stimulation, the animals are euthanized by exsanguination with 40 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monochromator and a spectrophotometer is used to quantify the amount of FITC-BSA in each sample. An excitation wavelength of approximately 490 nm is utilized and the emission intensity at 535 nm is determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion is an ipsilateral effect (i.e. occurs only on the side of the dura in which the trigeminal ganglion was stimulated). This allows the use of the other (unstimulated) half of the dura as a control. The ratio of the amount of extravasation in the dura from the stimulated side, over the amount of extravasation in the unstimulated side, is calculated. Control animals dosed only with saline, yield a ratio of approximately 2.0. In contrast, a compound which effectively prevented the extravasation in the dura from the stimulated side would yield a ratio of approximately 1.0

Example 1 was tested essentially as described above and was found to have an extravasation ratio of 1.12 at 10 mg/kg, 2 hours post po dose Example 7 was tested essentially as described above and was found to have an extravasation ratio of 1.18 at 10 mg/kg, 2 hours post po dose.

Thus, compounds of the present invention are shown to be useful in the treatment of pain, in particular migraine.

I claim:

1. A compound of the formula:

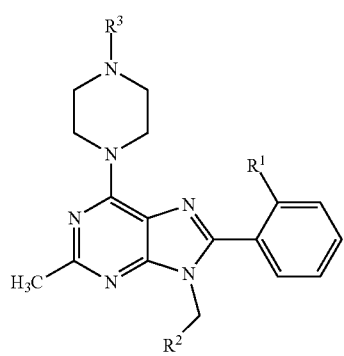

(I)

wherein;
$R^1$ is Cl or —$CH_3$;
$R^2$ is —C≡N, —$CH_2SO_2CH_3$, —$CONHCH_3$, —$CH_2NR^4R^5$, or —$CH_2C$≡N;
$R^3$ is $C_1$-$C_2$ alkyl, $C_1$-$C_2$ fluoroalkyl or —$C(O)CH_3$;
$R^4$ is H, —$C(O)CH_3$, —$CO_2CH_3$ or —$SO_2CH_3$; and
$R^5$ is H or combines with $R^4$ to form pyrrolidin-2-one;
or a pharmaceutically acceptable salt thereof.

2. The compound according to claim 1, or a pharmaceutically acceptable salt thereof, wherein $R^1$ is Cl.

3. The compound according to claim 1, or a pharmaceutically acceptable salt thereof, wherein $R^2$ is —$CH_2SO_2CH_3$, —$CH_2NR^4R^5$, or —$CH_2C$≡N.

4. The compound according to claim 1, or a pharmaceutically acceptable salt thereof, wherein $R^2$ is —$CH_2SO_2CH_3$.

5. The compound according to claim 1, or a pharmaceutically acceptable salt thereof, wherein $R^3$ is methyl, 2-fluoroethyl or —$C(O)CH_3$.

6. The compound according to claim 1, or a pharmaceutically acceptable salt thereof, wherein $R^3$ is methyl.

7. The compound according to claim 1, or a pharmaceutically acceptable salt thereof, wherein $R^5$ is H and $R^4$ is —$C(O)CH_3$ or —$CO_2CH_3$.

8. The compound according to claim 1, or a pharmaceutically acceptable salt thereof, wherein $R^1$ is Cl and $R^3$ is methyl.

9. The compound according to claim 1, or a pharmaceutically acceptable salt thereof, wherein $R^1$ is Cl and $R^3$ is methyl, 2-fluoroethyl or —$C(O)CH_3$.

10. The compound according to claim 1 being 8-(2-Chlorophenyl)-6-(4-methylpiperazin-1-yl)-2-methyl-9-(2-methylsulfonylethyl)purine, or a pharmaceutically acceptable salt thereof.

11. A pharmaceutical composition comprising a compound of the formula:

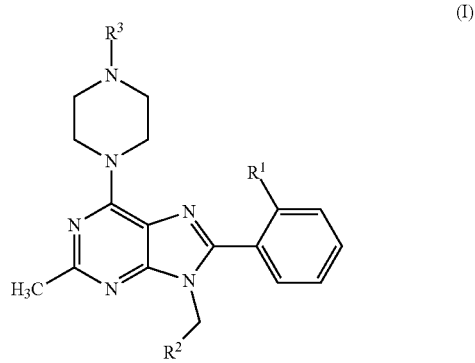

(I)

wherein;
$R^1$ is Cl or —$CH_3$;
$R^2$ is —C≡N, —$CH_2SO_2CH_3$, —$CONHCH_3$, —$CH_2NR^4R^5$, or —$CH_2C$≡N;
$R^3$ is $C_1$-$C_2$ alkyl, $C_1$-$C_2$ fluoroalkyl or —$C(O)CH_3$;
$R^4$ is H, —$C(O)CH_3$, —$CO_2CH_3$ or —$SO_2CH_3$; and
$R^5$ is H or combines with $R^4$ to form pyrrolidin-2-one;
or a pharmaceutically acceptable salt thereof, and a pharmaceutically acceptable diluent or carrier.

12. A method for the treatment of osteoarthritic pain or migraine, which comprises administering an effective amount of a compound of the formula:

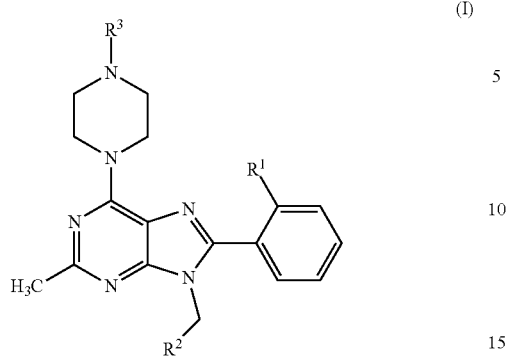

(I)

wherein;

R[1] is Cl or —CH$_3$;

R[2] is —C≡N, —CH$_2$SO$_2$CH$_3$, —CONHCH$_3$, —CH$_2$NR[4]R[5], or —CH$_2$C≡N;

R[3] is C$_1$-C$_2$ alkyl, C$_1$-C$_2$ fluoroalkyl or —C(O)CH$_3$;

R[4] is H, —C(O)CH$_3$, —CO$_2$CH$_3$ or —SO$_2$CH$_3$; and

R[5] is H or combines with R[4] to form pyrrolidin-2-one;

or a pharmaceutically acceptable salt thereof, to a human or animal in need thereof.

13. The method according to claim 12 wherein the compound is 8-(2-Chlorophenyl)-6-(4-methylpiperazin-1-yl)-2-methyl-9-(2-methylsulfonylethyl)purine, or a pharmaceutically acceptable salt thereof.

\* \* \* \* \*

UNITED STATES PATENT AND TRADEMARK OFFICE
CERTIFICATE OF CORRECTION

PATENT NO. : 8,710,063 B2  Page 1 of 1
APPLICATION NO. : 13/583009
DATED : April 29, 2014
INVENTOR(S) : Sean Patrick Hollinshead It is certified that error appears in the above-identified patent and that said Letters Patent is hereby corrected as shown below:

Title page, References Cited, Column 2 (Other Publications), Delete "yll-4-ethylamnino" and insert -- yl-4-ethylamino --, therefor.

Signed and Sealed this
Sixteenth Day of September, 2014

Michelle K. Lee
*Deputy Director of the United States Patent and Trademark Office*